United States Patent
Cohen et al.

(10) Patent No.: US 7,261,224 B2
(45) Date of Patent: Aug. 28, 2007

(54) ACCURATE DOSING PUMP AND ACCESSORIES THEREFOR

(75) Inventors: Ben Z. Cohen, 140 E. 80th St., New York, NY (US) 10021; Nigel Kelly, Rye, NY (US)

(73) Assignee: Ben Z. Cohen, New York, NY (US)

(*) Notice: Subject to any disclaimer, the term of this patent is extended or adjusted under 35 U.S.C. 154(b) by 0 days.

(21) Appl. No.: 10/467,904

(22) PCT Filed: Feb. 21, 2002

(86) PCT No.: PCT/US02/05864
§ 371 (c)(1),
(2), (4) Date: Feb. 2, 2004

(87) PCT Pub. No.: WO02/068317
PCT Pub. Date: Sep. 6, 2002

(65) Prior Publication Data
US 2004/0129734 A1    Jul. 8, 2004

Related U.S. Application Data

(60) Provisional application No. 60/270,330, filed on Feb. 21, 2001.

(51) Int. Cl.
*B67D 5/42* (2006.01)
(52) U.S. Cl. .................. 222/387; 222/388; 222/481.5
(58) Field of Classification Search ............... 222/386, 222/387, 388, 481.5
See application file for complete search history.

(56) References Cited

U.S. PATENT DOCUMENTS

| | | | |
|---|---|---|---|
| 2,781,953 A * | 2/1957 | Sylvander | 222/388 |
| 4,995,867 A * | 2/1991 | Zollinger | 604/514 |
| 5,190,191 A | 3/1993 | Reyman | |
| 5,340,289 A | 8/1994 | Konieczynski et al. | 417/430 |
| 5,556,268 A | 9/1996 | Topper et al. | 417/553 |
| 5,816,455 A | 10/1998 | Alpers et al. | |
| 5,957,338 A * | 9/1999 | Lehmann | 222/184 |
| 6,010,036 A | 1/2000 | Bougamont et al. | 222/183 |
| 6,158,621 A | 12/2000 | Keller | |
| 6,196,424 B1 | 3/2001 | Bougamont et al. | 222/321.9 |
| 6,467,579 B1 * | 10/2002 | Simon | 184/105.2 |

* cited by examiner

*Primary Examiner*—Joseph A. Kaufman
(74) *Attorney, Agent, or Firm*—Hoffmann & Baron, LLP

(57) ABSTRACT

With the subject invention, a pump may be formed that generally includes a reservoir formed to accommodate at least one fluid dose, and a fluid-collecting chamber in communication with the reservoir. The fluid-collecting chamber is located such that fluid from the reservoir is fed thereinto, preferably gravitationally. A piston is disposed to reversibly slide within at least a dose-control portion of the fluid-collecting chamber, and the piston is configured such that upon sliding within the dose-control portion, the piston seals or substantially seals the dose-control portion from other portions of the fluid collecting chamber. The piston is configured to displace a volume of fluid from the sealed or substantially sealed dose-control portion which is approximately equal to or greater than the volume of one of the doses of the pump. A nozzle is also provided which is located such that the fluid displaced by the piston from the dose-control portion is generally urged towards the nozzle.

24 Claims, 15 Drawing Sheets

US 7,261,224 B2

ACCURATE DOSING PUMP AND ACCESSORIES THEREFOR

This invention claims priority of U.S. Provisional Application No. 60/270,330, filed Feb. 21, 2001.

BACKGROUND OF THE INVENTION

This invention relates to pumps, and, more particularly, to pumps having accurately-controlled dosing.

In the prior art, pumps are used for various applications ranging from administration of health and beauty products (e.g., hand lotion) to lubricants. With the majority of pump applications, accurate volumetric control of a dose is not critical. Certain applications, however, have been developed which do require highly accurate dose control. For example, pumps have been developed which deliver microdoses of ophthalmic fluid medication (5 microliter–50 microliter), such as those disclosed in certain patents to some of the inventors herein: U.S. Pat. No. 5,152,435, issued Oct. 6, 1992; U.S. Pat. No. 5,881,956, issued Mar. 16, 1999; and, PCT Application No. PCT/US00/21206, filed Aug. 23, 2000. These references are incorporated by reference herein in their respective entireties. As can be appreciated with all drug dispensing technology accurately controlled dosing is absolutely necessary, particularly with small doses.

SUMMARY OF THE INVENTION

With the subject invention, various embodiments of a pump are provided having accurate control of a dose. The volume of the pump dosage can vary, although accurate control is particularly advantageous with microdosing.

With the subject invention, a pump may be formed that generally includes a reservoir formed to accommodate at least one fluid dose, and a fluid-collecting chamber in communication with the reservoir. The fluid-collecting chamber is located such that fluid from the reservoir is fed thereinto, preferably gravitationally. A piston is disposed to reversibly slide within at least a dose-control portion of the fluid-collecting chamber, and the piston is configured such that upon sliding within the dose-control portion, the piston seals or substantially seals the dose-control portion from other portions of the fluid collecting chamber. The piston is configured to displace a volume of fluid from the sealed or substantially sealed dose-control portion which is approximately equal to or greater than the volume of one of the doses of the pump. A nozzle is also provided which is located such that the fluid displaced by the piston from the dose-control portion is generally urged towards the nozzle.

Advantageously, with the pump of the subject invention, a simple design can be provided which has a limited number of critical dimensions controlling the dose amount. The volume of the fluid displaced from the dose-control portion of the fluid-collecting chamber controls or substantially controls the pump's dose. In a highly-desirable embodiment, the dose-control portion is cylindrically shaped having two dimensions: a diameter and a length. As such, manufacturing variations affecting the dose amount may be minimized with only two dimensions being implicated (and their respective tolerances) in controlling dosing. The dose-control portion may encompass other volumetric shapes, such as a parallelepiped or a cylinder with a hemispherical end, although additional dimensions (and, thus, additional set(s) of tolerances) may be implicated (e.g., a parallelepiped includes a rectangular cross-section where parallelism between two sets of edges must be maintained; thus, squareness as a third factor must be considered).

These and other features of the invention will be better understood through a study of the following detailed description and accompanying drawings.

BRIEF DESCRIPTION OF THE DRAWINGS

In the drawing figures, which are merely illustrative, and wherein like reference numerals depict like elements throughout the several views.

DETAILED DESCRIPTION OF THE INVENTION

Figure 1:
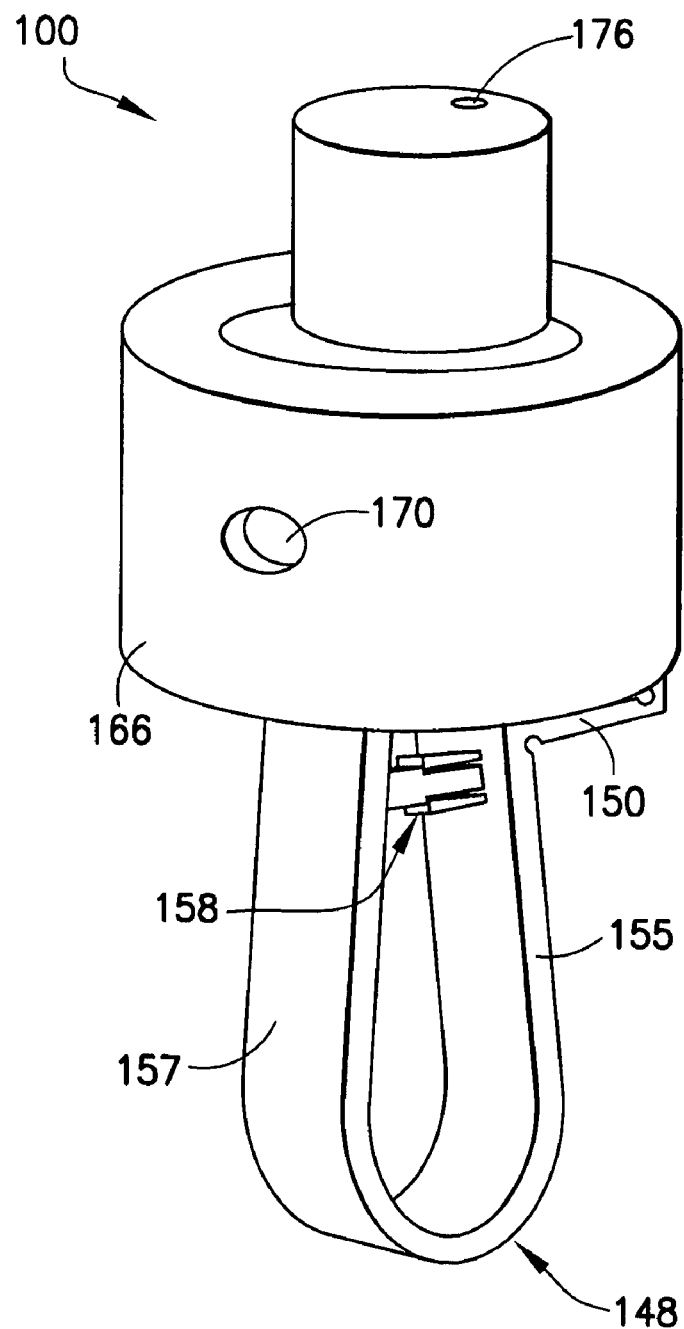
FIG. 1 is a perspective view of a first embodiment of a pump formed in accordance with the principles of the subject invention.

Various embodiments of an accurate dose control pump are described and depicted herein. As will be recognized by those skilled in the art, certain views in the drawings (e.g., FIGS. 2, 3, 4 and 9–13) are combination cross-sectional and cut-away views which illustrate the principles of the invention. Other pumping configurations consistent with the principles of the subject invention may be used.

Referring to FIGS. 1–4, a first embodiment of a pump formed in accordance with the principles of the subject invention is generally shown and designated with the reference numeral 100. The pump 100 includes a reservoir 112 and a fluid-collecting chamber 114, with the reservoir 112 being in communication, preferably open fluid communication, with the fluid-collecting chamber 114. As such, fluid accommodated within the reservoir 112 may be fed into the fluid-collecting chamber 114, preferably gravitationally. It is to be understood that, as used herein, the term "chamber" refers to a volume which may be open, partially enclosed, or wholly enclosed.

Figure 2:
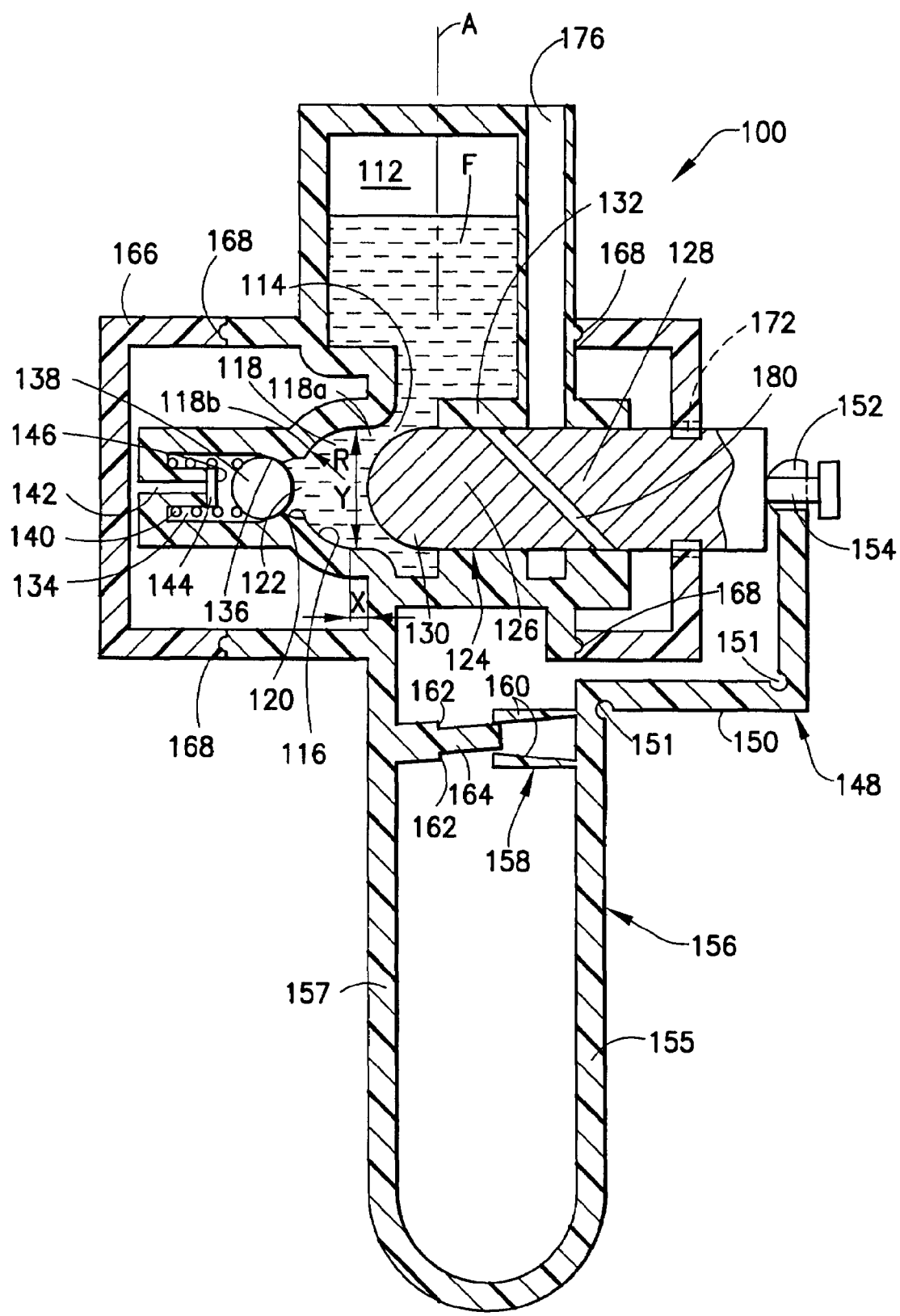
FIGS. 2–4 show a cross-section of the first embodiment of the pump in various operating stages.
Figure 3:
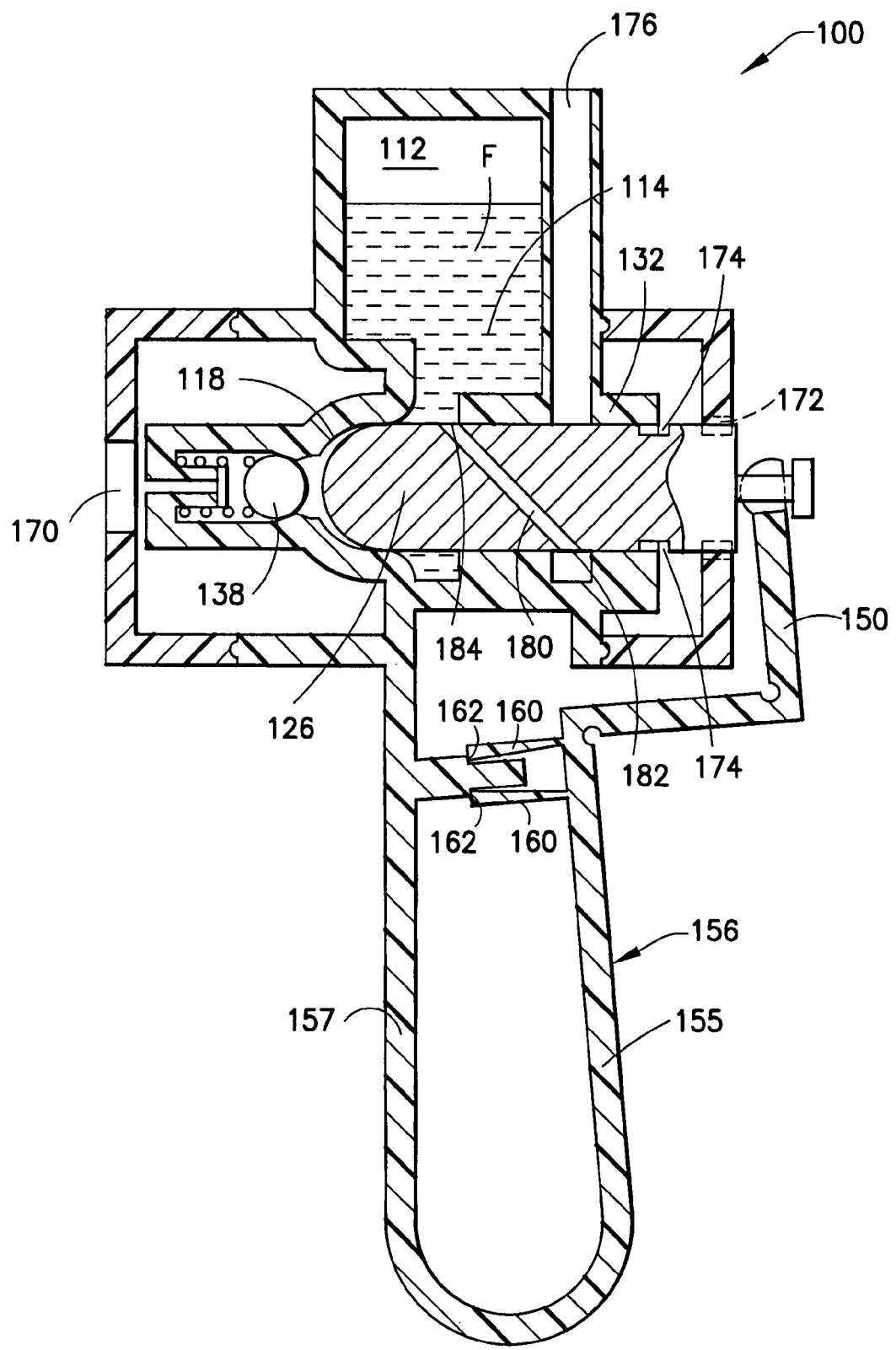
Figure 4:
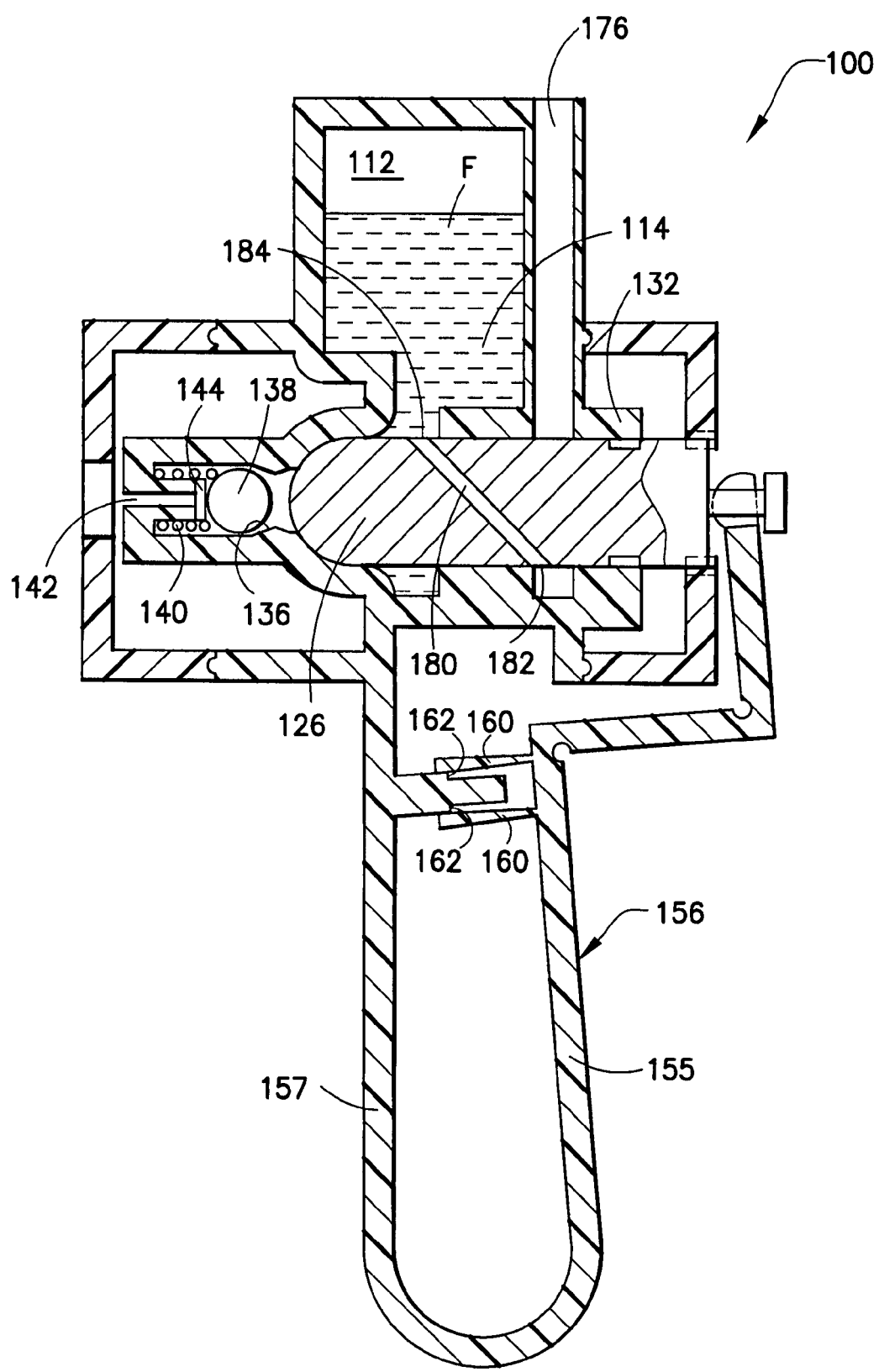

As shown in FIGS. 2–4, the fluid-collecting chamber 114 defines a piston seat 116 having a dose-control portion 118 with a first cylindrical part 118a, having a length of X and a diameter of Y, and a second hemispherical part 118b, having a radius of R. As described below, the dose-control portion 118 may have other configurations. The dose-control portion 118 terminates in an end portion 120, and a discharge aperture 122 is defined therein. It is preferred that the discharge aperture 122 be located centrally within the end portion 120.

A pump unit 124 is at least partially disposed within the fluid-collecting chamber 114. The pump unit 124 includes a piston 126 that is formed to seat within the piston seat 116; as shown in FIGS. 2–4, the piston 126 is formed with a cylindrical body 128 and an end 130 which dimensionally correspond to the parts 118a and 118b of the dose-control portion 118. The piston 126 may have other configurations.

The piston 126 is slidably disposed within a sleeve 132 that is defined in the body of the pump 100 and positioned to slide in and out of contact with the piston seat 116 defined by the fluid-collecting chamber 114. The sleeve 132 acts as a guide and support for the piston 126 in limiting sideward movement thereof. At rest, the piston 126 is spaced from the piston seat 116 and fluid F from the reservoir 112 floods the fluid-collecting chamber 114, acting under gravity (with the pump 100 being in an upright position).

Upon actuation, as described below, the piston 126 is caused to slide forward into the piston seat 116. It is critical for pressure to build up in the fluid which is trapped between the piston 126 and the piston seat 116 during operation. The piston 126 acts to seal or substantially seal the dose-control portion 118 from other portions of the fluid-collecting chamber 114 upon sliding into the dose-control portion 118. To this end, the end 130 of the piston 126 may be formed with a diameter slightly greater than the dose-control portion 118 of the piston seat 116 to prevent fluid from by-passing the piston 126 and returning to the fluid-collecting chamber 114 during operation. Alternatively, the end 130 of the piston 126 may be formed with a diameter slightly smaller than the dose-control portion 118 of the piston seat 116, where the fluid has sufficient inherent viscosity to create a seal about the piston 126. If the fluid does not have sufficient inherent viscosity, the end 130 of the piston 126 may still be formed with a diameter slightly smaller than the dose-control portion 118 of the piston seat 116; here, the piston 126 would be considered to substantially seal the dose-control portion 118 from other portions of the fluid-collecting chamber 114, if the amount of any fluid leaking back into the fluid-collecting chamber 114 is taken into account in providing proper dosages. With the end 130 creating a seal or substantial seal, the body 128 may be formed with a smaller diameter than the end 130. Optionally, the end 130 and/or the cylindrical body 128 may be formed with seal(s) (e.g., annular) for sealing the dose-control portion 118.

The dose-control portion 118 is in fluid communication with a discharge chamber 134 via the discharge aperture 122 and a tapered throat 136 which diverges from the discharge aperture 122 towards the discharge chamber 134. A regulator 138, such as a discharge outlet check valve (which may be in the form of a ball as shown in the Figures) is biased against the tapered throat 136 in a rest position, as shown in FIG. 2. Preferably, a coil spring 140 is used to generate the biasing force. In addition, it is preferred that a discharge nozzle 142 be formed to extend into the discharge chamber 134 having a cylindrical outer surface onto which the coil spring 140 is telescoped. An elongated slot 144 is defined in an end 146 of the discharge nozzle 142. The slot 144 is provided to ensure that the regulator 138 can never completely close off the entry into the discharge nozzle 142, thereby preventing the regulator 138 from throttling the outgoing fluid. The regulator 138 may be pressed against the end 146 with the slot 144 allowing the discharge nozzle 142 to communicate with the discharge chamber 134. The regulator 138 may be any valving element known to those skilled in the art which allows one-way flow, such as: a rubber diaphragm, or a spring-biased piston.

During actuation, the piston 126 is urged into the dose-control portion 118 thus sealing or substantially sealing the dose-control portion 118 from other portions of the fluid-collecting chamber 114 and allowing for a pressure rise in the fluid entrapped in the dose-control portion 118 (see FIG. 3). With further movement of the piston 126, the pressure of the fluid rises sufficiently to overcome the biasing force of the coil spring 140, and the regulator 138 yields to allow at least a portion of the entrapped fluid to exit the pump 100 via the slot 144 and the discharge nozzle 142. Upon discharge, the pressure of the entrapped fluid decays and the regulator 138 is eventually urged into contact with the tapered throat 136. (The regulator may operate in similar fashion to the outlet check valve disclosed in U.S. Pat. No. 5,881,956.) At rest, the check valve 138 is in pressing contact against the tapered throat 136 to prevent fluid from leaking out of the pump 100 due to the head of pressure from the reservoir 112. The piston 126 is returned to its rest position as explained below, and fluid re-charges the dose-control portion 118.

With the subject invention, a minimal number of tolerances can be utilized in controlling the dosing of the pump 100, thus, providing for accurate volumetric control of dosing. With typical prior art pumps, multiple dimensions are implicated in controlling dosing volume, with each dimension having its own set of manufacturing tolerance. With the configuration of FIGS. 2–4, the dimensions X, Y and R are implicated (assuming the piston 126 fully seats within the part 118b). Because the pumping action of the pump occurs with the movement of the piston 126 once the seal or substantial seal is formed, the volume of the displaced fluid is a function of the three dimensions X, Y and R.

Figure 5A:
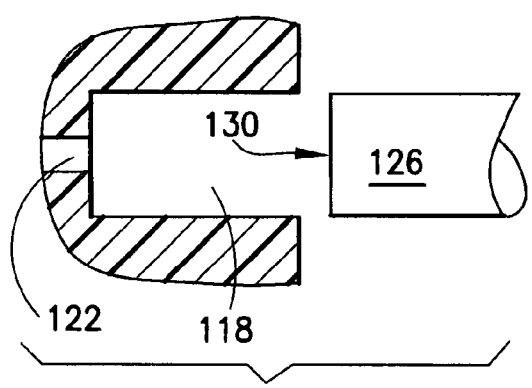
FIGS. 5a–5f show alternative configurations of the dose-control portion and the piston useable with the subject invention.
Figure 5B:
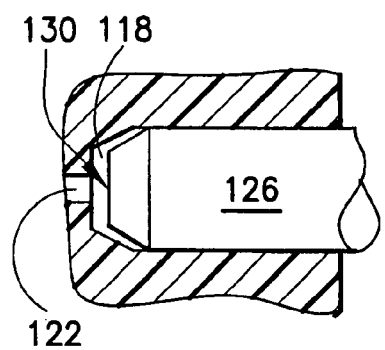
Figure 5C:
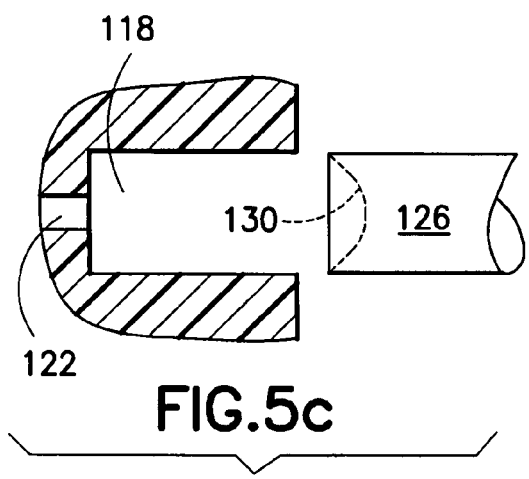
Figure 5D:
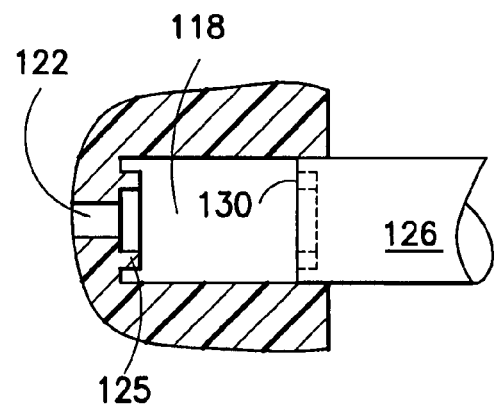

With the subject invention, the volume of the dose administered by the pump 100 is controlled by the volume of fluid displaced by the piston 126 from the dose-control portion 118. The dose-control portion 118 and the piston 126 may have various cooperating configurations. For example, with reference to FIG. 5a, the piston 126 and the dose-control portion 126 may be formed as right cylinders (i.e., with reference to the configuration of FIGS. 2–4, the radius R would be infinite). Other matching cross-sectional shapes are possible, such as, polygonal, elliptical, or irregular. Also, as shown in FIG. 5b, the dose-control portion 118 need not be straight and tubular, but may be frustoconical with the piston 126 matching. Also, the end 130 of the piston 126 may have various shapes, e.g., flat (as shown in FIG. 5a); convex (as shown in FIG. 5c); or, annular (as shown in FIG. 5d cooperating with an annular or discontinuous ring 125). Furthermore, the end 130 need not match the corresponding contour of the dose-control portion 118 (e.g., FIG. 5c).

Figure 5E:
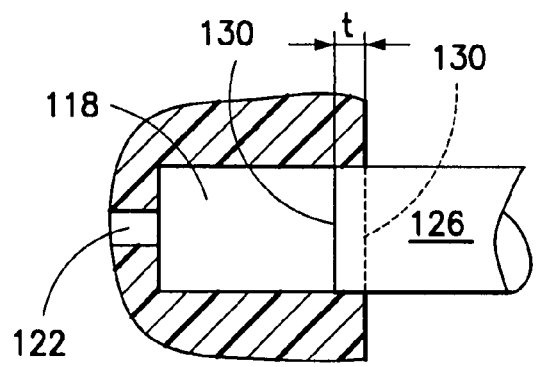

With reference to FIG. 5e, the piston 126 need not slide throughout the full length of the dose-control portion 118. Rather, as shown in dashed lines, the piston 126 may have a limited extent of movement "t". The extent of movement can be limited by creating a stop limiting the stroke of the piston (e.g. a shoulder) and/or by mismatching the end 130 of the piston 126 and the end of the dose-control portion 118. With the subject invention, the volume of the administered dose is equal (or approximately equal) to the volume of the fluid displaced by the piston 126. The displaced volume will generally be the volume swept by the end 130 of the piston 126 during movement from the point of formation of the seal or substantial seal with the dose-control portion 118 to the full extent of movement of the piston 126 within the dose control-portion 118 (i.e., the volume swept over the distance "t"). In certain circumstances, it may be desired to displace a volume of fluid from the dose-control portion 118 that is greater than the pump's dose of fluid to compensate for losses, compressive effects, and/or fluid entrapment along its route to the nozzle.

Figure 5F:
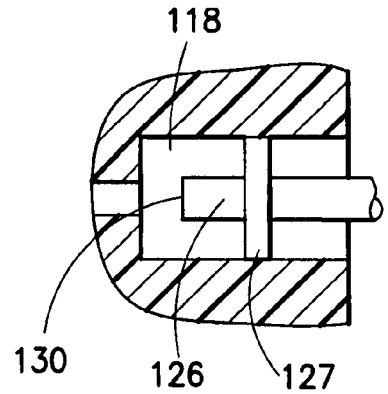

A critical element of the subject invention is the establishment of a seal or substantial seal with the dose-control portion 118. With reference to FIG. 5f, the seal may be formed at a location, or locations, spaced from the end 130 of the piston 126. Theoretically, the initial portion of the largest diameter section of the piston 126 entering the dose-control portion 118 will cause seal formation. With reference to the piston 126 of FIGS. 2–4, the piston 126 will theoretically seal the dose-control portion 118 upon the cylindrical body 128 initially entering the dose control portion 118. In practice, seal formation will generally occur past the theoretical point, due to dimensional differences, misalignment, fluid effects, friction, and so on. In an alternative arrangement, an enlarged piston region 127 spaced from the end 130 may be formed on the piston 126. The volume of fluid displaced by the enlarged position section 127 will be equal to (or approximately equal to) the volume of the dose.

As will be recognized by those skilled in the art, the principles described herein relating to the dose-control portion and the piston can be applied to various pump configurations, not just the embodiments disclosed herein.

Figure 6:
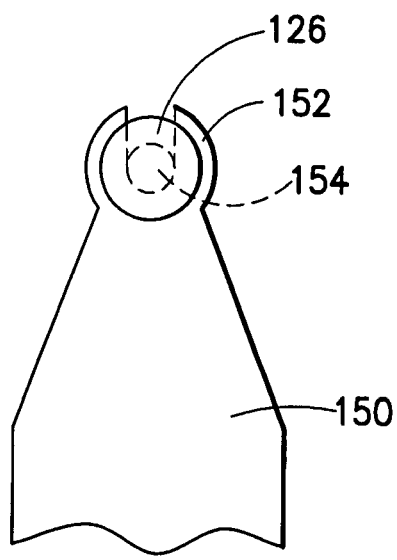
FIG. 6 shows a connection of a spring handle to the piston useable with the first embodiment.

The piston 126 slides freely within the sleeve 132 and is sealed (seals not shown) to prevent any leakage of the fluid at this interface. The piston 126 is returned to its rest position (spaced away from the dose-control portion 118) after actuation. In one exemplary manner of returning the piston 126, a spring handle 148 may be utilized. Here, free arm 150 of the spring handle 148 terminates at a split or forked ball end 152 (as shown in FIG. 6), which engages with a reduced diameter portion 154 that extends from the piston 126. Any method known to those skilled in the art may be used to connect the free arm 150 to the piston 126. The free arm 150 is weakened at certain points 151 to allow it to articulate freely and be pivotable so that it can be used to drive the piston 126 in and out relative to the sleeve 132. The free arm 150 may be provided with other rotatable connections to replace the points 151 to allow relative rotation between the various portions of the free arm 150 (e.g., hinged connections). In addition, the free arm 150 is formed with memory to have a rest position as shown in FIG. 2. The spring handle 148 is operated by squeezing a handle 156 connected to the free arm 150. An operator may wrap their fingers about the handle 156 to engage a rear part 155 of the handle 156 with their fingers while their thumb bears against a fixed front end 157 of the handle 156. The pump 100 is held to the eye with the front of the thumb resting on the cheek. The squeezing action causes inward deflection of the rear part 155, as shown in FIG. 4, and corresponding inward movement of the free arm 150 and the piston 126 in actuating the pump 100, as described above. By releasing the handle 156, the free arm 150 returns to its rest position with the piston 126 returning to its rest position. Other modes of returning the piston 126 to its rest position may be used, including a separate return spring pressing against the piston 126.

Preferably, a latch 158 is provided to ensure sufficient momentum is imparted in actuating the pump 100, as disclosed in U.S. Pat. No. 5,881,956. The latch 158 employs two cantilever members 160 which are formed and disposed to engage a pair of shoulders 162 on a front member 164. As such, the latch 158 resists force applied to the spring handle 148. Upon further force being applied to the spring handle 148, the cantilever members 160 ultimately snap outwardly of the shoulders 162 (at a predetermined threshold force) giving a "kick" to the pump 100 (see FIGS. 3 and 4). The "kick" ensures that a whole dose of the fluid is delivered (not a partial dose) and that the dose is delivered with sufficient momentum.

Figure 7:
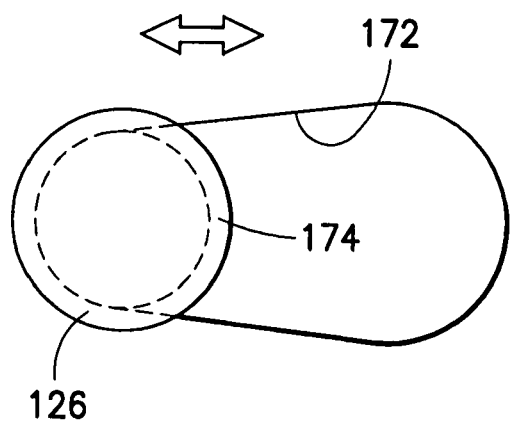
FIG. 7 is an elevational view of a tapered cut-out formed in a locking collar useable with the first embodiment.

Preferably, to limit the ingress of contaminants and/or to prevent unwanted actuation of the pump 100, a locking collar 166 is provided which is rotatably mounted to the pump 100. Any manner known to those skilled in the art may be used to mount the locking collar 166 such as using beads 168. The locking collar 166 is formed with an opening 170 and with a tapered cut-out 172 (FIG. 7). When the pump 100 is not in use, the locking collar 166 is rotated (about axis 'A' shown in FIG. 2) to bring the cut-out 172 into snap-on contact with channels 174 (which may be discontinuous or a single channel) formed towards the rear of the piston 126, as shown in FIG. 2. In this manner, the cut-out 172 prevents sliding movement of the piston 126. In addition, in the locked position, the opening 170 is out of alignment with the discharge nozzle 142 to protect against the ingress of dirt thereinto (FIG. 2). The locking collar 166 rotates into a use position, as shown in FIGS. 3 and 4, wherein the opening 170 aligns with the discharge nozzle 142 and the cut-out 172 does not engage the piston 126.

Figure 8:
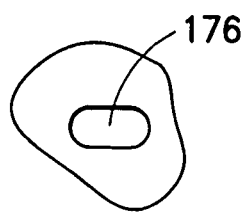
FIG. 8 is a top plan view of a vent slot useable with the first embodiment.

With the pump 100, the reservoir 112 is preferably vented to atmosphere. Here, a permanently opened vent slot 176 is set into the pump 100, (top view of slot 176 is shown in FIG. 8). The vent slot 176 may be of various cross-sectional shapes, such as an ellipse, With the pump 100, the reservoir 112 is preferably vented to atmosphere. Here, a permanently opened vent slot 176 is set into the pump 100, (top view of slot 176 is shown in FIG. 8). The vent slot 176 may be of various cross-sectional shapes, such as an ellipse, circle, polygon, or an irregular shape. The slot 176 also extends downwardly and about the piston 126. A cross vent 180 is defined in the piston 126 such that its ends are not in fluid communication with the vent slot 176 of the piston 126 at rest. Preferably, the cross vent 180 is sealed from the reservoir 112 by the sleeve 132 with the piston 126 at rest. Upon actuation, a first end 182 of the cross vent 180 comes into fluid communication with the vent slot 176 while a second end 184 of the cross vent is in fluid communication with the fluid-collecting chamber 114 (see FIGS. 3 and 4). The cross vent 180 only allows for venting to atmosphere when the piston 126 is urged towards the piston seat 116.

Figure 9:
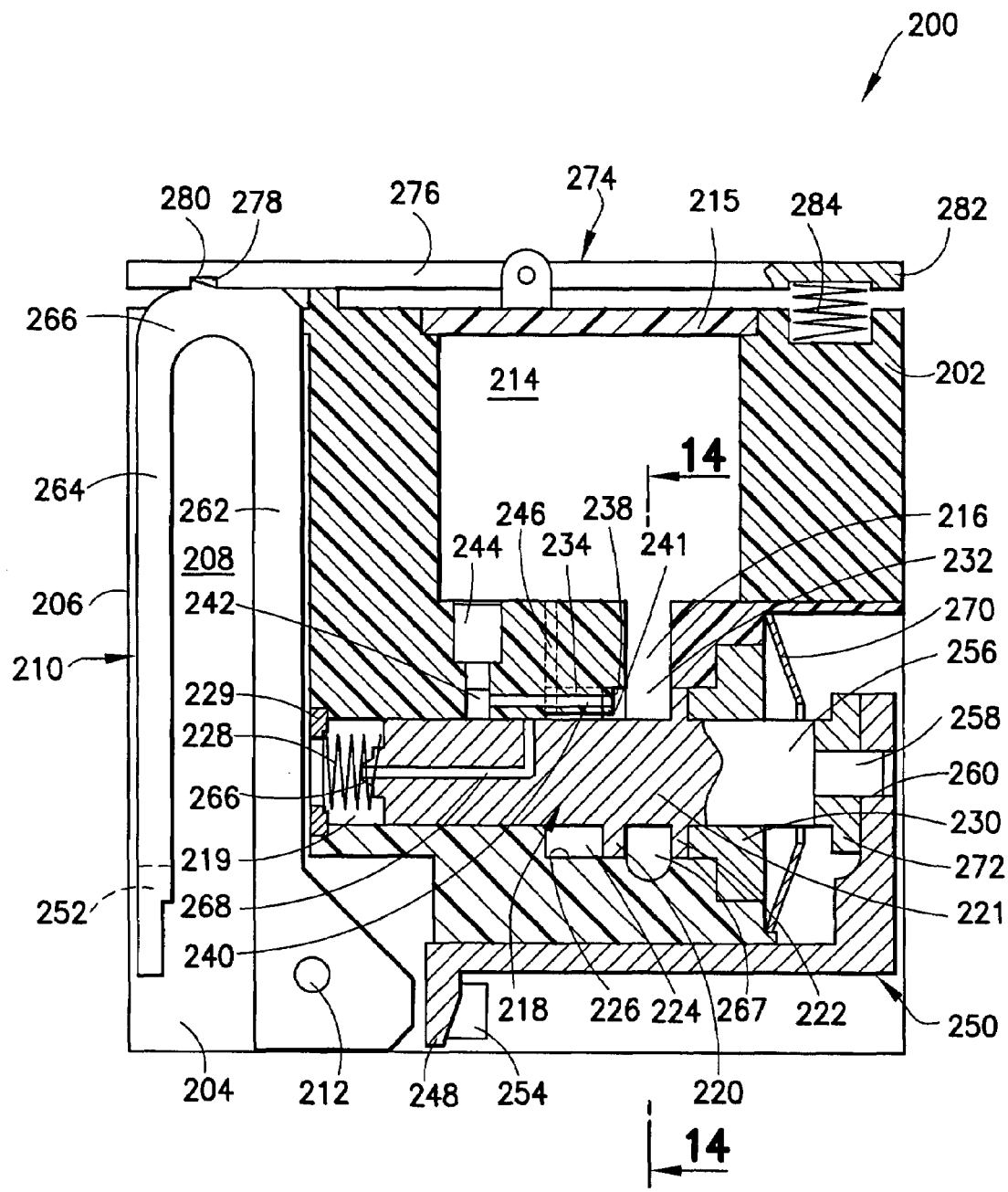
FIGS. 9–13 show a second embodiment of a pump formed in accordance with the principles of the subject invention in various operating stages.
Figure 10:
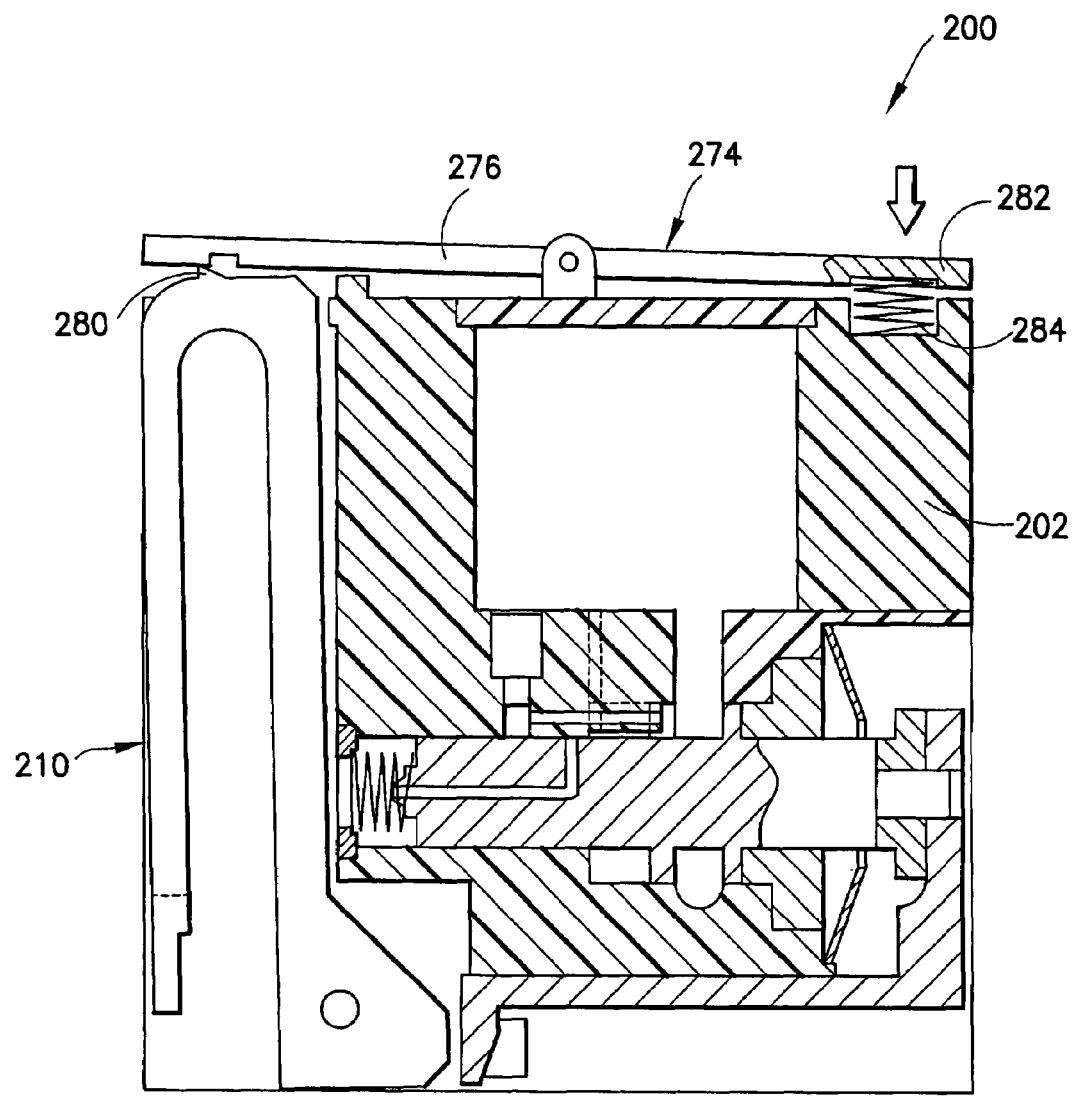

With reference to FIGS. 9–17, a second embodiment of a pump formed in accordance with the principles of the subject invention is shown and generally designated with the reference numeral 200. The pump 200 includes a housing 202 which is generally rectangular with side walls 204. The housing 202 is preferably set back from front edges 206 of the side walls 204 such that a recess 208 is defined. The recess 208 advantageously may accommodate a handle 210 used for actuating the pump 200. The handle 210 is connected to the side walls 204 by a rotatable connection 212 which may be a hinge pin. As shown in FIG. 9, it is preferred that the handle 210 be dimensioned so that in a stowed, non-use position the handle 210 is wholly accommodated within the recess 208. As will be described in more detail below, the handle 210 is rotated downwardly about the rotatable connection 212 when readied for use.

The housing 202 includes a reservoir 214 for accommodating fluid and a fluid-collecting chamber 216 which is in communication with the reservoir 214, preferably in open fluid communication. A separate insert 215 may be mounted to the housing 202 to allow for charging of the reservoir 214 and/or for easing manufacturing of the pump 200. As with the first embodiment, fluid within the reservoir 214 is fed into the fluid-collecting chamber 216, preferably gravitationally.

A piston 218 is disposed to slide within a piston passage 219 that passes through a portion of the fluid-collecting chamber 216. The interfaces of the piston 218 and the piston passage 219 are sealed in any known manner to prevent leakage from the pump 200. The piston includes spaced-apart front and rear bulkheads 220 and 222, respectively, extending from a cylindrical body 221. The bulkheads 220 and 222 have a spool-like configuration trapping an annular volume of fluid therebetween and about the cylindrical body 221. The bulkheads 220, 222 are generally disc-shaped and preferably conform to the contour of a dose-control portion 224 that is in communication with the fluid-collecting chamber 216, and that is defined within a bore 226 that encircles the piston 218. The bulkheads 220, 222 are formed to seal or substantially seal in the same manner as described above with respect to the piston 126.

A spring 228 is provided to bias the piston 216 into a rest position as shown in FIG. 9 with the rear bulkhead 222 being spaced from the dose-control portion 224. The spring rests against a ring 229 that extends into the piston passage 219. A stop 230 engages the rear bulkhead 222 in limiting the rearward movement of the piston 216 caused by the spring 228. The stop 230 may be recessed to accommodate the rear bulkhead 222 in avoiding blockage of a throat 232 of the fluid-collecting chamber 216 which communicates the reservoir 214 with the dose-control portion 224.

To facilitate manufacturing of the pump 200, the stop 230 may be formed separately from the housing 202 so that an opening is initially formed in communication with the piston passage 219. The spring 228 and the piston 216 may be inserted into the housing 202 through the opening, and, thereafter, the stop 230 may be secured to the housing 202 using any technique known to those skilled in the art.

Figure 14:
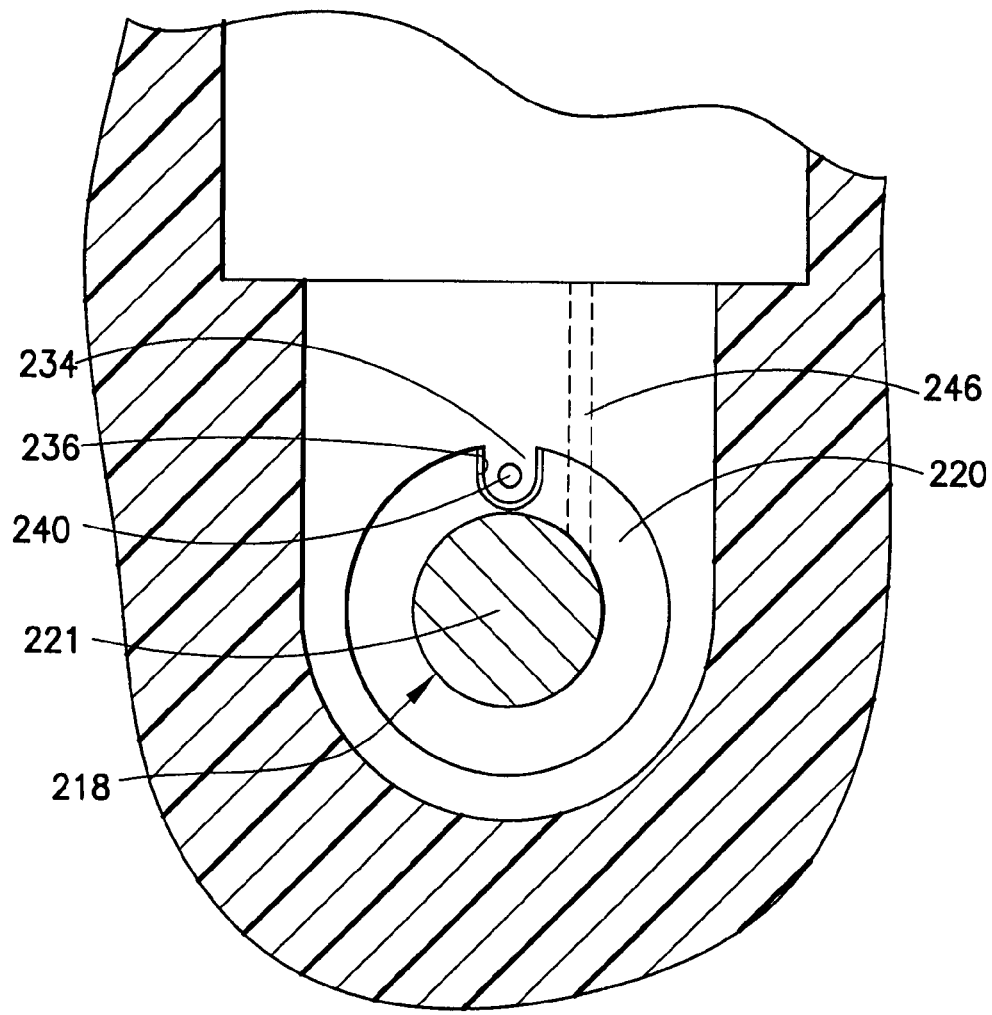
FIG. 14 is a partial cross-sectional view taken along line 14—14 of FIG. 9.
Figure 15:
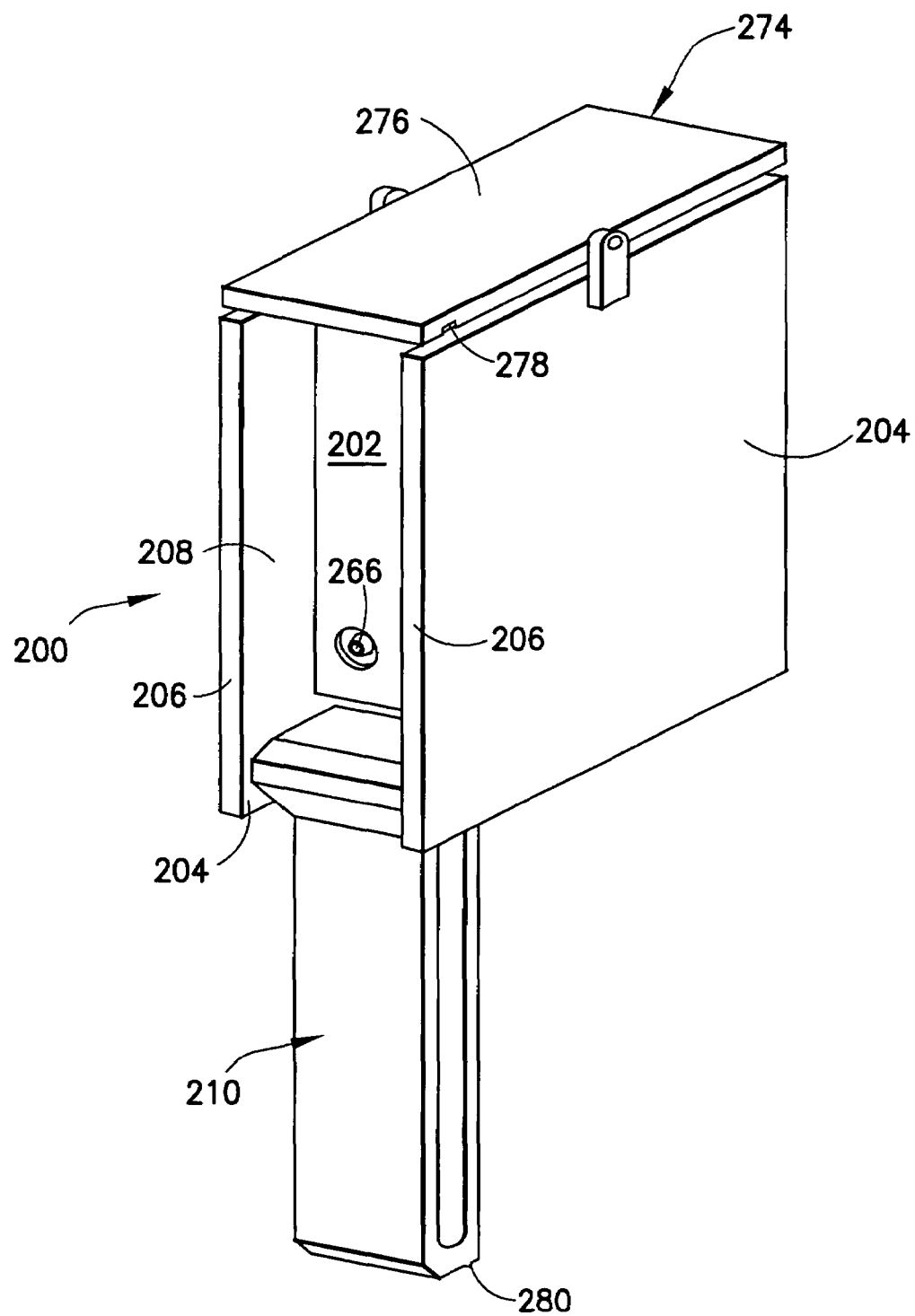
FIG. 15 is a perspective view of the second embodiment of the invention.

An elongated rib 234 is provided which extends from the bore 226. With reference to FIG. 14, the front bulkhead 220 includes a notch 236 which conforms to the cross-sectional shape of the rib 234. As described below, the notch 236 allows the front bulkhead 220 to translate relative to the rib 234. The rib 234 terminates at an end 238 which is spaced from the throat 232. A rib passage 240 extends from the end 238, throughout the rib 234 and into communication with the piston passage 219 via a vertical port 242. Preferably, a slot 241 extends into the end 238 to prevent complete shut-off of the rib passage 240 and to avoid fluid throttling into the rib passage 240. To ease manufacturing of the pump 200, the vertical port 242 may be formed by a tool passing through the reservoir 214 and, thereafter, sealed with a plug 244. A vent 246 is also formed to communicate the piston passage 219 (at a location forward of the front bulkhead 220 and preferably near the end of the bore 226) with the reservoir 214. The vent 246 allows for release of fluid pressure due to compressive effects of the front bulkhead 220, as described below.

To ready the pump 200 for use, the handle 210 is rotated downwardly and caused to engage free end 248 of actuating arm 250. To obtain a tight securement between the handle 210 and the free end 248, the handle 210 is formed with a notched slot 252 that snaps about button 254. The connection between the handle 210 and the free end 248 must be releasable to allow the handle 210 to be rotated upwardly into its stowed position. With the notched slot 252, upon rotating the handle 210 upwardly, the notched slot 252 will deflect and release from the button 254. Any method of releasably connecting the handle 210 and the free end 248 known to those skilled in the art may be utilized.

The actuating arm 250 is secured to an end 256 of the piston 218, preferably outside of the piston passage 219. An interference fit between a pin 258 extending from the end 256 and an aperture 260 may be used. The actuating arm 250 is configured with a general Z-shape so that general sideward movement of the free end 248 will result in corresponding sliding movement of the position 218.

Figure 11:
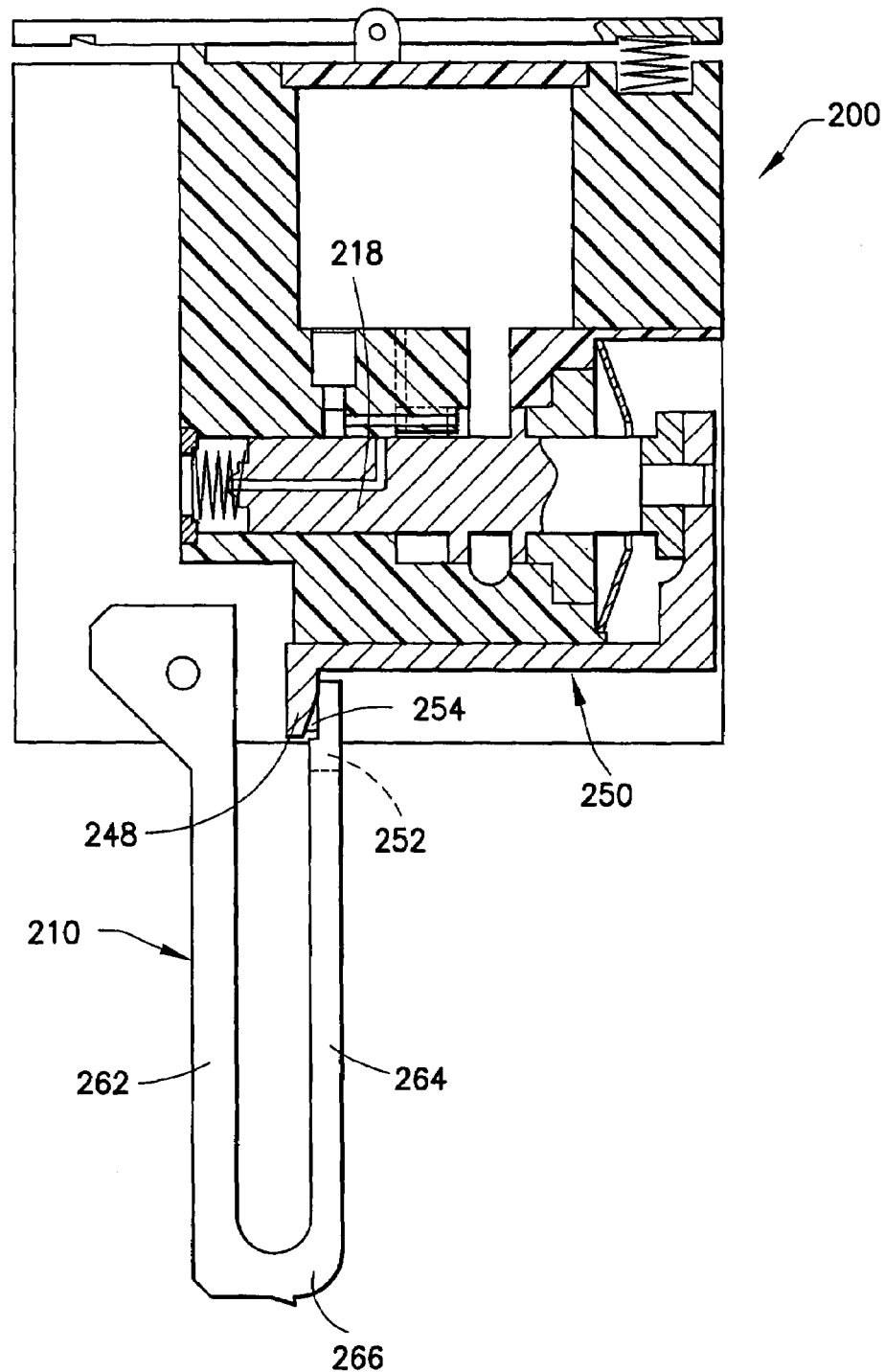
Figure 12:
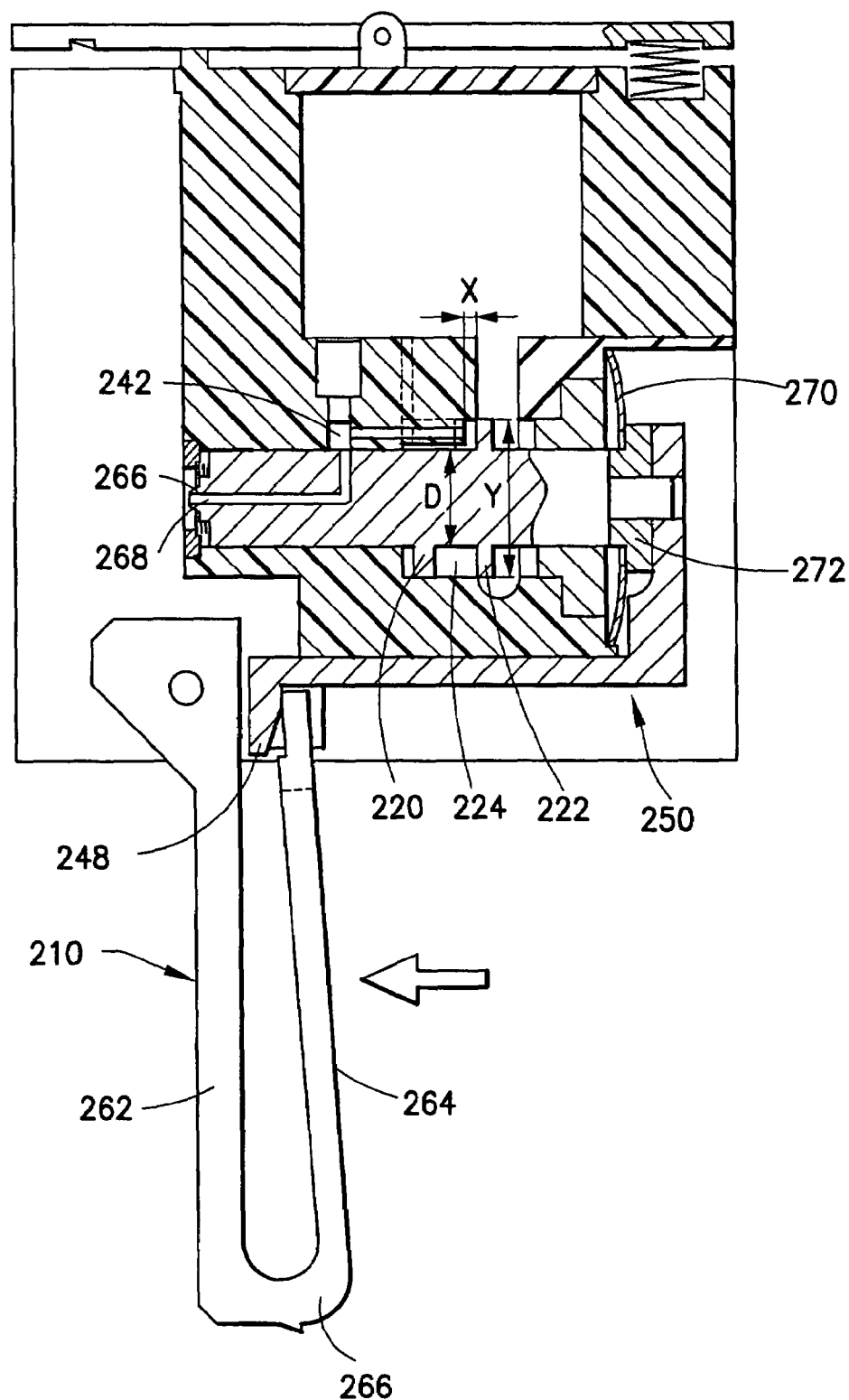
Figure 13:
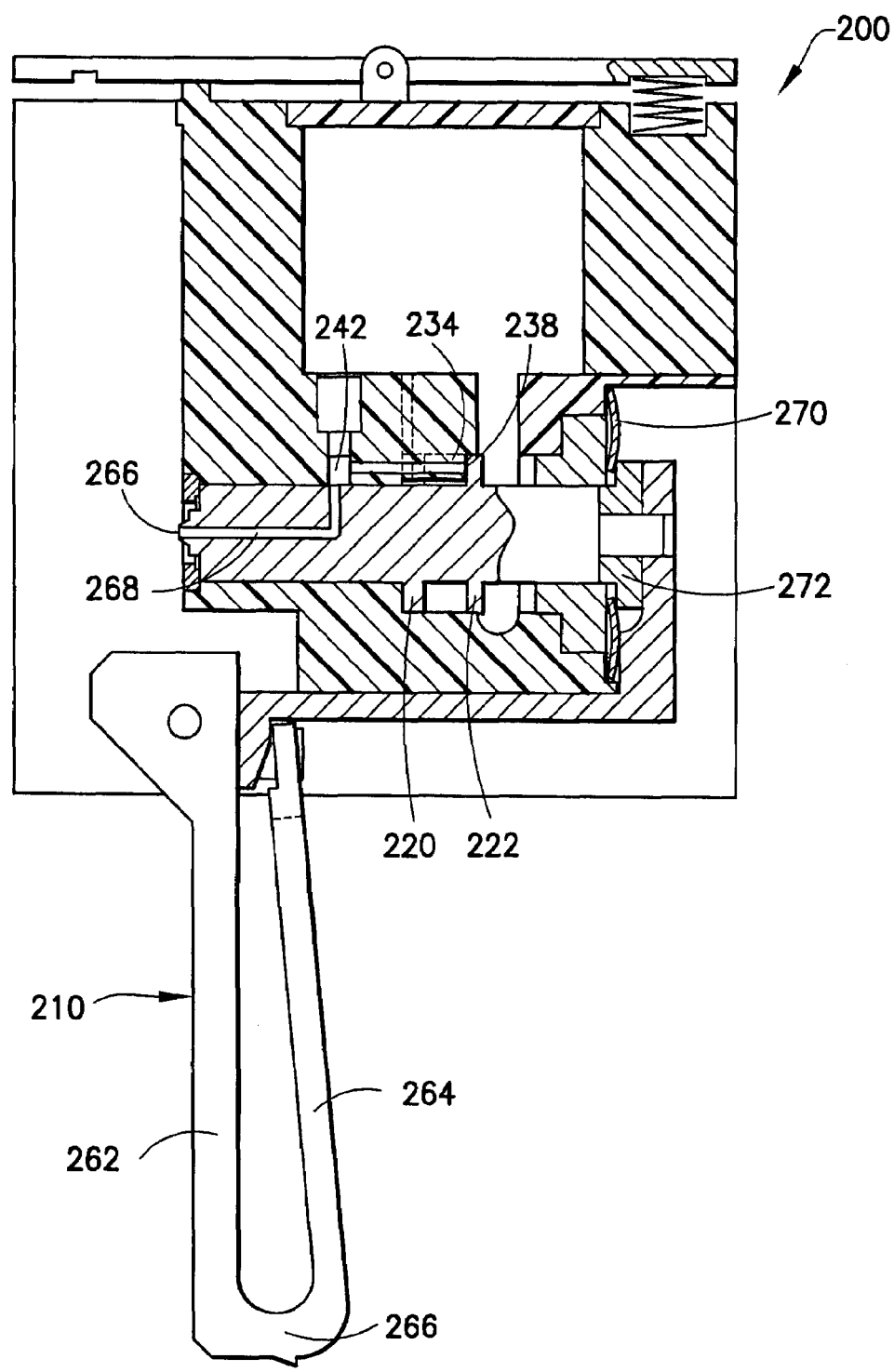

In use, the handle 210 is caused to engage the free end 248. Although not shown, the handle 210 may be formed fixed to the free end 248 and not foldable into the recess 208. The handle 210 preferably has a U-shape with sides 262 and 264 being connected about a bottom 266. To actuate the pump 200, the side 264 is pressed inwardly (i.e., deflected towards the side 262) causing sideward movement of the free end 248. As shown in FIGS. 11–13, the movement of the free arm 248 results in sliding movement of the piston 218.

In a rest state, as shown in FIGS. 9 and 11, fluid is trapped between the bulkheads 220 and 222. Upon sliding movement of the piston 218, the entrapped fluid is also moved. The front bulkhead 220 translates along the length of the rib 234 compressing fluid trapped forwardly of it. The pressure of this trapped fluid is released through the vent 246.

Upon the rear bulkhead 222 passing the throat 232 and entering the dose-control portion 224, the rear bulkhead 222 causes the dose-control portion 224 to be sealed or substantially sealed from other portions of the fluid-collecting chamber 216. Theoretically, the rear bulkhead 222 will seal or substantially seal the dose-control portion 224 upon initial entry, as shown in FIG. 12. In practice, the seal or substantial seal will generally be generated with the rear bulkhead 222 having further translated into the dose-control portion 224. Unlike the front bulkhead 220, the rear bulkhead 222 has no notch corresponding to the rib 234, but rather is a solid disc that has a sealing effect fully circumferentially about the dose-control portion 224. With further translation of the rear bulkhead 222, over the length X (FIG. 12), fluid is displaced from the dose-control portion 224 through the rib passage 240. The end 238 of the rib 234 may act as a stop in preventing further translation of the rear bulkhead 222 in defining the end of the length X and/or the front bulkhead 220 may engage the end of the bore 226 (FIG. 13).

The piston 218 is formed with a nozzle 266 and a nozzle passage 268 that is in communication therewith. The nozzle passage 268 is formed to align with the vertical port 242 while the rear bulkhead 222 translates the length X. As such, the dose-control portion 224 is brought into fluid communication with the nozzle 266 to allow fluid displaced from the dose-control portion 224 to be dispensed through the nozzle 266. Once fluid is dispensed, the handle 210 may be released, and the piston 218 returns to its rest position by force of the spring 228 and memory of the handle 210. Also, the reservoir 214 is vented by air being drawn into the nozzle 266 after fluid dosing. The air reaches the reservoir 214 through the vent 246 and/or the throat 232. Fluid re-charges the fluid-collecting chamber 216 from the reservoir 214. A trough 267 may also be provided to minimize resistance in movement of the piston 218. Beneficially, the second embodiment does not require a regulator between the nozzle 266 and the dose-control portion 224, because with the piston 218 at rest, the nozzle 266 is not in communication with the dose-control portion 224.

As described above, the volume of the fluid displaced from the dose-control portion is approximately equal to or greater than one dose of fluid to be administered by the pump 200. With this embodiment, three dimensions are implicated in controlling the volume of the displaced fluid. The length X; the diameter Y of the dose-control portion 224; and, the diameter D of the cylindrical body 221 of the piston 218 (see FIG. 12). In accordance with the discussion above, the configuration of the piston 218, the bulkheads 220, 222 and the dose-control portion 224 may be varied, as will be recognized by those skilled in the art.

As additional features, a latch 270 may be provided in accordance with the disclosure of U.S. Pat. No. 5,881,956 to ensure sufficient momentum is imparted to the pump 200 in causing actuation thereof. The latch 270 acts against shoulders 272 which may be formed as a collar mounted on the piston 218, unitarily with the piston 218, or unitarily with the actuating arm 250. The latch 270 Will resist movement of the piston 218 until sufficient force is applied to overcome the resistance of the latch 270.

Additionally, a release mechanism 274 may be provided to release the handle 210 from its stowed position. Because of the recessed construction, the handle 210 may be difficult to access when in a stowed position. The release mechanism includes a strip 276 that is pivot mounted to the housing 202. At one end of the strip 276, a notch 278 is formed to receive and engage a detent 280 that extends from the bottom 266 of the handle 210. The notch 278 is located to maintain the handle in a stowed portion within the recess 208. A second end 282 of the strip 276 is spaced from the housing 202 so as to be moveable relative thereto. By depressing the second end 282, the strip 276 is rotated and the notch 278 caused to separate from the detent 280. As a result, the handle 210 drops at least partially out of the recess 208 under the effect of its own weight (eccentrically created movement about the rotatable connection 212). A spring 284 is preferably provided between the housing 202 to bias the second end 282 upwardly such that the notch 278 is urged into a rest position allowing for engaging the detent 280.

Figure 16:
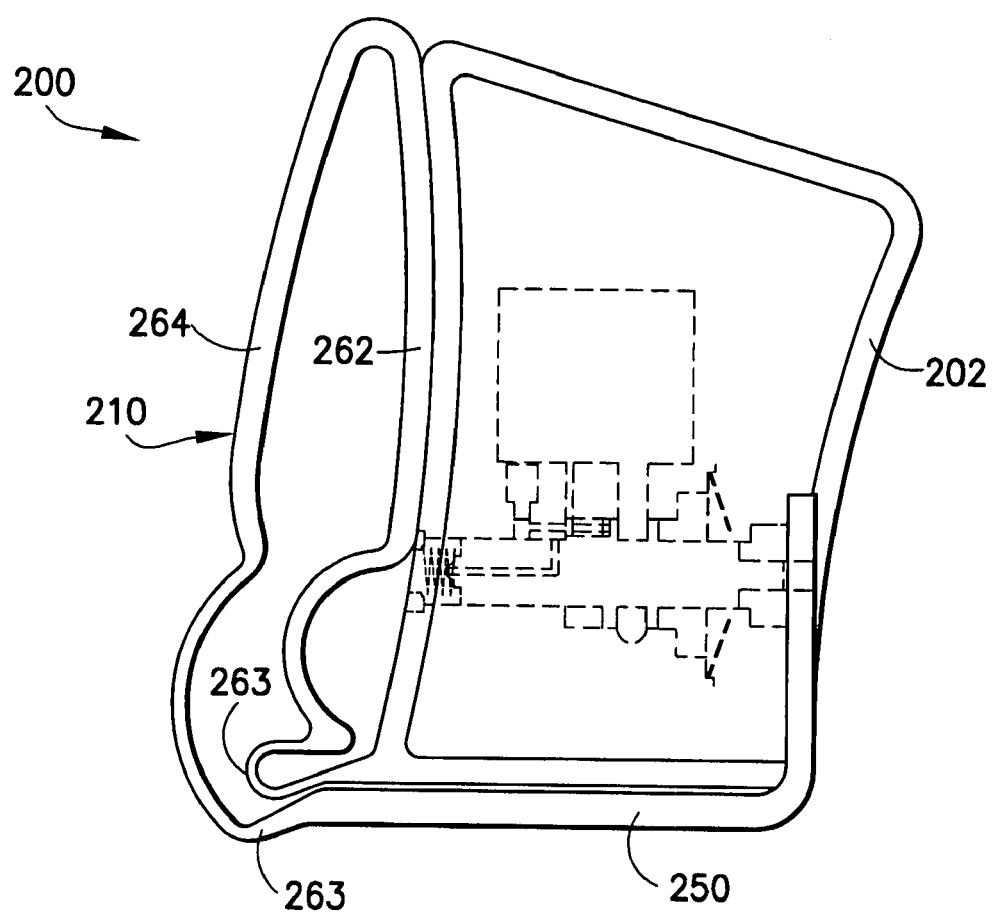
FIGS. 16 and 17 show an alternative handle and housing configuration of the second embodiment of the invention.
Figure 17:
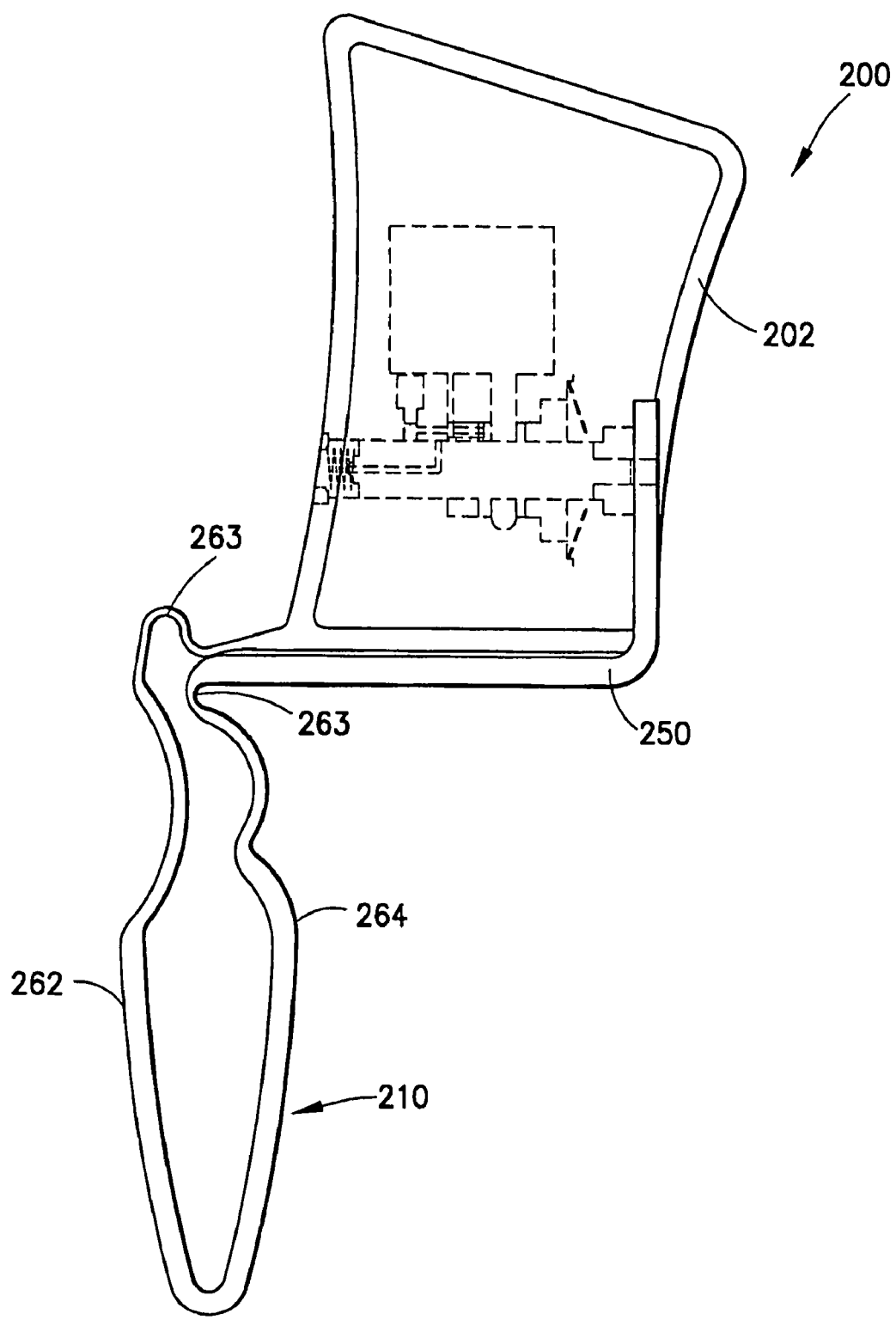

As a variation of the second embodiment, and with reference to FIGS. 16 and 17, the handle 210 may be hingedly connected to the housing 202 using living hinges 263. Here, the side 264 of the handle 210 is formed unitarily with the actuating arm 250. Advantageously, in all variations, the handle 210 may block the ingress of contaminants into the nozzle 266. The recess 208 need not be provided with this variation. In all other respects, this variation functions in the same manner as described above.

Elements, described herein, are preferably formed of thermoplastic compatible with the fluid contents of the pump. Certain elements such as coil springs may be metallic, although may also be polymeric.

Pumps utilizing the principles disclosed herein may be used to administer various volumetric doses. The principles are particularly advantageous with microdosing pumps for administering ophthalmic fluids and fluid medications which may be, and/or which may include, any of the following:

I. anti-glaucoma/intra-ocular pressure lowering (IOP) compounds such as:
   a.) alpha-adrenoceptor blocking agents, e.g., apraclonidine, brimonidine, AGN 192836, AGN 193080, etc.
   b.) beta-adrenoceptor blocking agents, e.g., carteolol, betaxolol, levobunolol, metipranolol, timolol, vaninolol, adaprolol, etc.
   c.) miotics, e.g., pilocarpine, carbachol, physostigmine, etc.
   d.) sympathomimetics, e.g., adrenaline, dipivefrine, etc.
   e.) carbonic anhydrase inhibitors, e.g., acetazolamide, dorzolamide, etc.; and,
   f.) prostaglandins, e.g., PGF-2 alpha or its prodrug latanoprost;
II. diagnostic fluids, such as anesthetics and medications to dilate the eye;
III. anti-inflammatory agents (both steroid and non-steroid);
IV. artificial tears and eye whiteners; and
V. antibiotics.

As is readily apparent, numerous modifications and changes may readily occur to those skilled in the art, and hence it is not desired to limit the invention to the exact construction operation as shown and described, and accordingly, all suitable modification equivalents may be resorted to falling within the scope of the invention as claimed.

What is claimed is:

1. A pump for administering doses of fluid, said pump comprising:
   a reservoir formed to accommodate at least one of the doses of fluid;
   a fluid-collecting chamber in communication with said reservoir;
   a piston disposed to reversibly slide within at least a dose-control portion of said fluid-collecting chamber, wherein, with the pump being in a quiescent state, said piston not sealing or substantially sealing said dose-control portion from other portions of said fluid-collecting chamber, wherein, upon actuation of the pump, said piston seals or substantially seals said dose-control portion from other portions of said fluid-collecting chamber with said piston sliding within said dose-control portion, and wherein said piston being configured to displace a volume of fluid from said sealed or substantially sealed dose-control portion which is approximately equal to or greater than the volume of one of the doses of fluid;
   an actuator engageable to cause movement of said piston and actuation of said pump, said actuator being configured to be engaged at a location spaced from said piston to cause movement of said piston;
   a nozzle, wherein said nozzle being located such that fluid displaced by said piston from said dose-control portion is generally urged towards said nozzle; and
   a regulator disposed between said dose-control portion and said nozzle to selectively control flow therebetween, wherein, upon actuation of the pump, said regulator being initially in a closed state.

2. A pump as in claim 1, wherein said volume of said dose-control portion is defined by two dimensions.

3. A pump as in claim 2, wherein a first of said dimensions is an axial length of said dose-control portion.

4. A pump as in claim 3, wherein a second of said dimensions is a diameter of said dose-control portion.

5. A pump as in claim 2, wherein said dose-control portion is solely defined by said two dimensions.

6. A pump as in claim 5, wherein said dose-control portion has a cylindrical shape.

7. A pump as in claim 5, wherein said dose-control portion has a tubular shape.

8. A pump as in claim 1, wherein said regulator is a check valve.

9. A pump as in claim 8, wherein said check valve is spring-biased to close communication.

10. A pump as in claim 1, wherein said reservoir is vented ambiently.

11. A pump as in claim 10, further comprising a blind vent passageway, wherein a through-bore is formed in said piston, said through-bore communicating said vent passageway and said reservoir upon said piston sliding a predetermined extent within said dose-control portion.

12. A pump as in claim 1, wherein said dose-control portion being in communication with said nozzle via at least one exit passageway, said at least one exit passageway being located to communicate said nozzle and said dose-control portion with said dose-control portion being sealed or substantially sealed from said reservoir by said piston.

13. A pump as in claim 12, wherein a portion of said exit passageway is defined in said piston.

14. A pump as in claim 1, wherein said fluid-collecting chamber is in open fluid communication with said reservoir.

15. A pump as in claim 1, wherein fluid from said reservoir is gravitationally fed into said fluid-collecting chamber.

16. A pump as in claim 1, wherein said actuator is a handle connected to said piston such that compression of said handle causes movement of said piston.

17. A pump as in claim 16, wherein said handle is rotatable.

18. A pump as in claim 1, wherein said piston includes at least two spaced-apart bulkheads, said bulkheads partially defining a volume in communication with said fluid-collecting chamber with said piston not sealing or substantially sealing said dose-control portion.

19. A pump as in claim 18, at least one of said bulkheads sealing or substantially sealing said dose-control portion with said piston sliding within said dose-control portion.

20. A pump as in claim 18, wherein a rib protrudes into said dose-control portion, a first of said bulkheads having a notch conforming to the cross-sectional shape of said rib, said notch allowing said first bulkhead to translate within said dose-control portion relative to said rib.

21. A pump as in claim 20, wherein a second of said bulkheads having a disc shape, said second bulkhead configured to seal or substantially seal said dose-control portion with said piston sliding within said dose-control portion.

22. A pump as in claim 1, wherein said piston is spaced from said dose-control portion with the pump being in a quiescent state.

23. A pump as in claim 1, wherein said piston is unitary.

24. A pump as in claim 1, wherein all portions of said piston which reversibly slide through said fluid-collecting chamber are continuously contained within said pump.

* * * * *

UNITED STATES PATENT AND TRADEMARK OFFICE
CERTIFICATE OF CORRECTION

PATENT NO.         : 7,261,224 B2                                           Page 1 of 1
APPLICATION NO.    : 10/467904
DATED              : August 28, 2007
INVENTOR(S)        : Cohen et al.

It is certified that error appears in the above-identified patent and that said Letters Patent is hereby corrected as shown below:

Column 3, line 11, replace "...movement thereof At rest, the..." with --movement thereof. At rest, the...--.

Column 7, line 7, replace "...in any known maimer to prevent..." with --in any known manner to prevent...--.

Column 9, line 14, replace "The latch 270 Will resist movement...." with --The latch 270 will resist movement...--.

Signed and Sealed this

Twenty-seventh Day of November, 2007

JON W. DUDAS
*Director of the United States Patent and Trademark Office*